(12) United States Patent
Gharagozloo

(10) Patent No.: US 8,377,454 B2
(45) Date of Patent: Feb. 19, 2013

(54) TREATING MALE INFERTILITY SECONDARY TO SPERM OXIDATIVE STRESS

(76) Inventor: Parviz Gharagozloo, Pennington, NJ (US)

( * ) Notice: Subject to any disclaimer, the term of this patent is extended or adjusted under 35 U.S.C. 154(b) by 286 days.

(21) Appl. No.: 12/771,928

(22) Filed: Apr. 30, 2010

(65) Prior Publication Data

US 2010/0278939 A1    Nov. 4, 2010

Related U.S. Application Data

(60) Provisional application No. 61/174,732, filed on May 1, 2009.

(51) Int. Cl.
*A61K 9/00* (2006.01)

(52) U.S. Cl. ........ 424/400; 424/451; 424/464; 424/641; 424/702

(58) Field of Classification Search ................ None
See application file for complete search history.

(56) References Cited

U.S. PATENT DOCUMENTS

| 5,863,940 | A |  | 1/1999 | Cavazza |  |
|---|---|---|---|---|---|
| 2002/0142052 | A1 | * | 10/2002 | Trant | 424/729 |
| 2003/0148016 | A1 | * | 8/2003 | Choudhry | 426/660 |
| 2005/0002992 | A1 | * | 1/2005 | McCleary et al. | 424/439 |
| 2007/0104762 | A1 | * | 5/2007 | Roizen | 424/439 |
| 2008/0213401 | A1 | * | 9/2008 | Smith | 424/657 |
| 2009/0081177 | A1 |  | 3/2009 | Tremellen |  |

FOREIGN PATENT DOCUMENTS

WO    2007/003007 A1    1/2007

OTHER PUBLICATIONS

Fertilix™ from TESS search on US trademark website, published Oct. 10, 2006; pp. 1-2.*

Gharagozloo et al., "The role of sperm oxidative stress in male fertility and the significance of oral antioxidant therapy," Human Reproduction (2011); vol. 0, pp. 1-13.

Ashok Agarwal, PhD, HCLD "Role of Oxidative Stress in Male Infertililty and Antioxidant Supplementation" Business Briefing: US Kidney & Urological Disease (2005).

Agarwal et al., "What an andrologist/urologist should know about free radicals and why," Urology (2006); 67:2-8.

Twigg et al., "Analysis of the impact of intracellular reactive oxygen species generation on the structural and functional integrity of human spermatozoa: lipid peroxidation, DNA fragmentation and effectiveness antioxidants," Human Reproduction (1998); vol. 13, No. 6, pp. 1429-1436.

Sharlip et al., "Best practice policies for male infertillity," Fertility and Sterility (May 2002); vol. 77, No. 5, pp. 873-882.

Kumar et al., "Drug Therapy for Idiopathic Male Infertility: Rationale Versus Evidence," The Journal of Urology (Oct. 2006); vol. 176, pp. 1307-1312.

Tremellen et al., "Oxidative stress and male infertility—a clinical perspective," Human Reproduction Update (2008); vol. 14, No. 3, pp. 243-258.

Cost Science, http://coastscience.com/totalfertility (last visited: May 3, 2011).

Cost Science, http://costscience.com/mfs (last visited: May 3, 2011).

Proxeed, http://www.proxeed.com/order.asp (last visited: May 3, 2011).

Pack 3 Fertimax + 3 Oocyte + − 10 €—Fertility, http://fertimax.net/male-female-fertility/5-pack-3-fertimax-3-oocyte-10-euros.html (last visited: May 3, 2011).

Agarwal et al., "Prevention of oxidative stress injury to sperm," Journal of Andrology (Nov. 1, 2005): vol. 26, No. 6, pp. 654-660.

* cited by examiner

*Primary Examiner* — Bethany Barham

(74) *Attorney, Agent, or Firm* — Fox Rothschild LLP; Shahnam Sharareh

(57) ABSTRACT

A profertility composition for administration to infertile men with sperm oxidative stress is disclosed. The composition comprises a unique combination of a pharmaceutically acceptable vitamin E, vitamin C, selenium, zinc, folic acid, lycopene and at least one carnitine source.

11 Claims, No Drawings

TREATING MALE INFERTILITY SECONDARY TO SPERM OXIDATIVE STRESS

CROSS-REFERENCE TO RELATED APPLICATIONS

This application claims priority to U.S. Provisional Patent Application No. 61/174,732 filed May 1, 2009, the contents of which is hereby incorporated by reference in its entirety.

FIELD OF INVENTION

The present invention relates to methods, compositions and fertility kits used to enhance the natural fertility potential of men. The present invention utilizes naturally occurring antioxidants as to provide a prophylactic treatment of sperm oxidative stress. Additionally, the novel products described herein further include vitamins and minerals for improving semen parameters enhancing the overall health of sperm thus increasing, fertilization rates, number of viable embryos, pregnancy rates and reducing miscarriages.

BACKGROUND

Male infertility has been on the rise for several decades and is now considered a major health problem affecting around one in twelve of the men in USA. Id. If the trends observed over the last century continues, some infertility experts predict that by the middle of this century, most men will be advised to freeze their sperm at a young age to ensure adequate sperm quality.

A successful fertilization and subsequent embryo development requires properly matured sperm chromatin with minimal damage to its DNA integrity. Equally important, is the integrity of sperm membrane lipid structure essential for sperm motility and sperm-oocyte fusion. At least one of the causes of sperm DNA damage and membrane peroxidation is attributed to excess Reactive Molecular Species ("RMS"), most importantly Reactive Oxygen Species ("ROS"), leading to a condition commonly referred to as sperm oxidative stress. In general, the term "Oxidative Stress" refers to a condition that occurs as a result of excessive generation of ROS and/or a diminished capacity of ROS scavenging endogenous antioxidants. Accordingly, the excess concentration of ROS overwhelms the local environmental antioxidant defense mechanism of the spermatozoa potentially leading to the formation of sperm cells with lower or no fertilizing potential.

Under normal conditions, cells utilize an array of enzymatic and non-enzymatic antioxidants as internal defense to scavenge and neutralize excess levels of ROS. It is believed that oxidative stress develops either because of an overabundance of ROS from environmental or pathological stressors or a lack of antioxidant capacity to neutralize excess concentrations of ROS. Excess ROS within semen and the sperm cell has been described to cause degradation of the cellular components such as membrane and DNA, hence, the sperms injured by such oxidative species have diminished or no fertility potential.

To date several studies have reported that levels of ROS within semen can be reduced by augmenting the scavenging capacity of seminal plasma using oral antioxidant supplementation. In fact, the benefits of oral antioxidant therapy has been described in numerous articles. By the way of reference, such articles include Comhaire et al, The Effects of Combined Conventional Treatment, Oral Antioxidants and Essential Fatty Acids on Sperm Biology in Subfertile Men, Prostaglandins Leuko Essent Fatty Acids, 63, 159-165 (2000); Lenzi et al, Placebo-Controlled, Double-blind, Cross-over Trial of Gluthathione therapy in male infertility, Hum Reprod, 8, 1657-1662 (1993); Greco et al, Reduction of the Incidence of Sperm DNA Fragmentation by Oral Antioxidant Treatment. J Androl, 17, 276-287 (2005); Tremellen et al, A Randomised Control Trial Examining the Effect of an Antioxidant (Menevit) on Pregnancy Outcome During IVF-ICSI Treatment, Australian and New Zealand Journal of Obstetrics and Gynecology 47, 216-221 (2007); and Agarwal et al, Oxidative stress, DNA Damage and Apoptosis in Male Infertility, a Clinical Approach, BJU Int, 95, 503-507 (2005), the teachings of which are incorporated herein in their entirety.

However, there is no product in the market today that has the instantly disclosed combination of antioxidants, minerals and vitamins. Moreover, the prior art does not teach the steps described herein to enhance the natural fertility process. At least one object of the present invention is to address such a need in the field.

Excessive concentration of ROS can cause extensive sperm DNA damage and membrane peroxidation. In general ROS includes reactive moieties such as hydroxyl radicals ($OH^-$), ionic species such as superoxide anions ($O_2^-$), and neutral but highly reactive oxidizing molecules such hydrogen peroxides ($H_2O_2$). In semen, such species are predominantly generated by leukocytes or morphologically abnormal sperms. It has been described in the art that ROS plays both physiological and pathological roles in maturation of sperm cells. For example, at normal baseline ROS concentrations, sperms are properly matured as ROS modulates the regulation of the normal sperm function in various cascades including but not limited to sperm-oocyte fusion, acrosome reaction and sperm capacitation.

On the other hand, excess ROS concentrations result in direct insult on cellular components such as lipids, proteins and DNA, thus interfering with normal cell function. Traditional semen analysis methodologies fail to detect DNA damage caused by ROS. In fact, in many cases infertile men who undergo a clinical workup show normal sperm parameters, including sperm count motility and morphology. However, when compared with healthy fertile men, at least a subpopulation of these infertile men, show higher concentrations of oxidants in their seminal fluid which may be coupled with significantly lower concentrations of antioxidant as compared to healthy fertile men.

At the genomic level, excess concentrations of ROS modifies sperm DNA structure in a number of ways. For example, ROS can induce chromatin cross-linking, DNA base oxidation and cause high frequencies of single and double DNA strand breaks. Even though, sperms with damaged DNA may still fertilize the oocyte, the degree of DNA damage can have profound implications in normality of embryonic development resulting in higher miscarriage rates, birth defects or the long-term health of the progeny.

Current medical approach to facilitate embryonic development and pregnancy uses invasive techniques collectively referred to as Assisted Reproductive Techniques ("ART"), including Intrauterine Insemination ("IUI"), In vitro Fertilization ("IVF") and Intracytoplasmic Sperm Injection ("ICSI"). However, such techniques generally have an average rate of success of about 30%. At least one explanation for such poor outcome is the fact that the semen and the sperm analysis techniques employed during ART cannot differentiate sperms with DNA damage from the normal ones.

Moreover, ART modes of fertilization have been linked with birth defects and incidences of childhood cancer, e.x. acute leukemia and lymphoma. Nevertheless, ART remains the only viable option for infertile couples. Another shortcoming of the ART is the cost. Couples on average undergo several IVF attempts to achieve a pregnancy, therefore undertaking huge expenses. Additionally, the risk of failure often causes intense emotional trauma.

Moreover, ART can not and does not address the damage done by ROS to sperm and ultimately to the fertilized egg. Therefore, there is a need in the art to address the impact of Sperm Oxidative Stress ("SOS") among infertile couples. Currently, there are no effective and generally accepted pharmacotherapy that can combat the problem of male infertility associated with SOS. Thus, there is a need for convenient, inexpensive fertility methodologies and products to aid and improve couple's fertility potential. There is also a need for a kit that will provide couples in need with all products, tools and material required to facilitate a comprehensive plan for achieving a successful pregnancy.

SUMMARY OF THE PRESENT INVENTION

The present invention fills the foregoing need by lowering and prophylactically treating SOS by boosting the non-enzymatic antioxidant defense mechanism. The invention comprises unique combinations of several natural antioxidants, vitamins and minerals clinically tried for efficacy to improve sperm health and quality. The invention is therefore intended to be a prophylactic treatment to improve the overall health of sperms thus improving the sperm-oocyte fertilization, reducing miscarriage rates and improving pregnancy rates.

This invention provides methods of using combinations of naturally occurring antioxidant molecules for treating infertility in men predominantly suffering from SOS alone or in combination with aromatase inhibitors, suitable anti-inflammatory, and/or antibiotics.

At least one aspect of the present invention is directed to a method of increasing the rate of pregnancy in a female subject by administering to the male partner an effective amount of a combination of anti-oxidants, vitamins and minerals, for at least a period of up to about three (3) months prior to any fertilization attempts, wherein said combination is substantially free of vitamin A, vitamin K and/or garlic. In at least one embodiment of this aspect of the invention, the combination includes at least one source of vitamin C, at least one source of vitamin E, at least one source of carnitine, lycopene and at least one source of folic acid.

In a more preferred embodiment of this aspect of the invention, the combination includes at least one source of vitamin C, at least one source of vitamin E, at least one source of carnitine, and at least one source of folic acid, at least one mineral which is selenium, zinc, magnesium or combinations thereof, wherein the composition is free of any traces of vitamin A, vitamin K and/or garlic.

In another aspect of the present invention, a novel method of reducing ROS damage to sperm DNA by at least 2.5% as compared with placebo, including the steps of administering to a male subject for at least a period of up to about three (3) months an effective amount of the combination of anti-oxidants, vitamins and minerals disclosed herein, wherein the combination is free of vitamin A, vitamin K and/or garlic.

In at least one embodiment of this aspect of the invention, the method of inhibiting ROS damage to sperm DNA cause a reduction in a measurement of DNA fragmentation secondary to SOS by at least 1%, 2.5%, 5%, 8%, 10%, 12.5%, 15%, 20%, 30% and preferably higher when compared to a placebo treatment. In another embodiment, the sperm DNA fragmentation is assessed by such technique including but not limited to Sperm Chromatin Dispersion ("SCD") test, Sperm Chromatin Structure Assay ("SCSA"), DNA Breakage Detection-Fluorescentce In Situ Hybridization ("DBD-FISH") test, Terminal Deoxyribonucleotidyl Transferase-Mediated dUTP Nic-End Labelling ("TUNEL") assay and 8-hydroxy-deoxyguanosine Assay ("8-OH-dG Assay").

Another aspect of the present invention provides for a method of treating an infertile male subject with sperm oxidative stress including the steps of (a) ascertaining the degree of DNA damage in said male subject, as measured by SCSA, TUNEL, SCD, DBD-FISH, or 8-OH-dG Assay, (b) initiating a course of therapy by administering an effective amount of a combination of anti-oxidants, vitamins and minerals and free of vitamin A, vitamin K and/or garlic for at least a period of three (3) months, (c) reascertaining the degree of DNA damage in said male subject post the therapy of the step (b), and (d) fertilizing the egg of the female partner with said male subject's sperm after completion of the treatment course of step (b), wherein the degree of the DNA damage measurement is reduced or otherwise improved, as compared to placebo or said subject's own pretreatment values by at least 1%, 2.5%, 5%, 8%, 10%, 12.5%, 15%, 20%, 30%, and preferably higher.

Another aspect of the present invention provides for a method of treating an infertile couple including the steps of (a) determining the couples susceptibility to oxidative stress, (b) initiating the combination regimen disclosed herein for the male partner wherein the male partner receives an effective amount of a combination of anti-oxidants, vitamins and minerals and free of vitamin A, vitamin K and/or garlic for at least a period of three (3) months. In another aspect of the present invention, the female partner may independently or simultaneously with the male partner receive the anti-oxidant therapy optionally including an alpha-lipoic acid regimen.

The present invention also provides a method of reducing the concentration of ROS generated by leukocytes in the reproductive tract and/or semen of a male subject, the method including the steps of administering to the male subject (a) an effective amount of the antioxidant, vitamin and mineral combination for at least a period of three (3) months and (b) an effective amount of an aromatase inhibitor agent or an appropriate antibiotic.

The present invention also provides a method of improving sperm function in a male subject, the method including the steps of administering to the male subject an effective amount of the combination described herein for at least a period of three (3) months.

The present invention also provides for a method of improving quality of an embryo produced by fertilization of an oocyte by a sperm from a male subject, wherein the male subject has completed a three (3) month course of antioxidant regimen comprising receiving a combination of at least one source of vitamin C, at least one source of vitamin E, at least one source of carnitine, and at least one source of folic acid, at least one mineral which is selenium, zinc, magnesium or combinations thereof, wherein the regimen is free of any traces of vitamin A, vitamin K and/or garlic.

In at least one embodiment of this aspect of the invention, methods of prophylactically reducing the risk of forming a nonviable zygote comprising administering to a male subject in need thereof, a composition comprising an effective amount of a combination of at least one source of vitamin C, at least one source of vitamin E, at least one source of carnitine, and at least one source of folic acid, at least one mineral which is selenium, zinc, magnesium or combinations thereof, wherein the regimen is free of any traces of vitamin A, vitamin K and/or garlic, and optionally an effective dose of an aromatase inhibitor or an antibiotic.

The present invention also provides a composition comprising an effective amount of at least one source of vitamin C, an effective amount of at least one source of vitamin E, an effective amount of at least two sources of carnitine, and an effective amount of at least one source of folic acid, at least one mineral which is selenium, zinc, magnesium or combinations thereof wherein the composition is substantially free of any traces of vitamin A, vitamin K and/or garlic. In a preferred embodiment of this aspect of the invention, the composition only contains an effective amount of at least a source of vitamin C, an effective amount of at least one source of vitamin E, an effective amount of L-carnitine, propionyl-L-carnitine or acetyl-L-carnitine or combinations thereof, and an effective amount of at least one source of folic acid, an effective amount of lycopene, and an effective amount of at least one mineral which is selenium, zinc, magnesium or combinations thereof, wherein the composition is free of any traces of vitamin A, vitamin K and/or garlic.

In a preferred embodiment of this aspect of the present invention, inventor discloses a composition that contains vitamin E, vitamin C or a suitable salt thereof, folic acid, lycopene, a carnitine source, selenium, and zinc in pharmaceutically acceptable forms wherein the formulation is substantially free of vitamin A and vitamin K and/or garlic or any extracts thereof.

In a more preferred embodiment of this aspect of the invention the composition is composed of vitamin E in about 100-800 IU; vitamin C about 50-800 mg, or an equivalent salt thereof; selenium in about 25-100 μg; zinc in about 10-35 mg; folic acid in about 0.25-0.75 mg; lycopene about 3-12 mg; and a carnitine source in about 250-4000 mg, wherein the formulation is substantially free of vitamin A and vitamin K and/or garlic or any extracts thereof. In yet another embodiment of the present invention, the carnitine source is a prodrug for carnitine.

In the preferred embodiment of the present invention the composition includes vitamin E in about 200 IU; vitamin C in about 90 or 200 mg, selenium in about 55 μg; zinc in about 15 mg; folic acid in about 0.5 mg; lycopene about 5 mg; and acetyl-L-carnitine in about 1000 mg. In yet another embodiment, the composition includes vitamin E in about 200 IU; vitamin C in about 200 mg, selenium in about 55 μg; zinc in about 15 mg; folic acid in about 0.5 mg; lycopene about 5 mg; and propionyl-L-carnitine in about 500 mg, and acetyl-L-carnitine in about 1000 mg.

Another aspect of the present invention is directed to the disclosed antioxidant containing compositions, wherein the compositions are in the form of a tablet, a capsule, a powder mixture, a paste, a suspension, a solution, an elixir, a topical or an oral patch, or a parenteral preparation. In at least on embodiment of this aspect of the invention, the composition contains sustain or extended release components, immediate release components, microparticles, nanoparticles and suitable excipients to enhance the bioavailability of the product as compared to their respective conventional preparations. In the preferred embodiment of this aspect of the invention, the antioxidant containing composition can be administered orally, via an inhaler, or via the parenteral route.

In another aspect of the present invention, pregnancy kits are provided comprising a set of pregnancy tests, articles for storage of specimens, and compositions containing vitamin E in about 200 IU; vitamin C in about 90 or 200 mg, selenium in about 55 μg; zinc in about 15 mg; folic acid in about 0.5 mg; lycopene about 5 mg; and acetyl L-carnitine in about 500 mg and/or compositions containing vitamin E in about 200 IU; vitamin C in about 90 or 200 mg, selenium in about 55 μg; zinc in about 15 mg; folic acid in about 0.5 mg; lycopene about 5 mg; and propionyl-L-carnitine in about 500 mg.

In at least another aspect of the present invention, pregnancy kits can comprise additional adjuvant agents such as aromatase inhibitors, glutathiones, or Coenzyme Q10, each of which may be administered separately or in combination with the antioxidant, mineral and vitamin combinations instantly disclosed.

The present invention also provides a method of isolating sperm and/or measuring DNA fragmentation from a male subject, the method including the steps of (a) administering to the male subject an effective amount of at least one source of vitamin C, an effective amount of at least one source of vitamin E, an effective amount of at least one source of carnitine, and an effective amount of at least one source of folic acid, an effective amount of lycopene, at least one mineral which is selenium, zinc, magnesium or combinations thereof wherein the composition is substantially free of any traces of vitamin A, vitamin K and/or garlic and (b) measuring the subject's sperm's DNA fragmentation index.

DETAILED DESCRIPTION OF THE PREFERRED EMBODIMENTS

Unless defined otherwise, all technical and scientific terms used herein have the same meaning as is commonly understood by one of skill in the art to which this invention belongs and shall be understood to have the meanings described below. All publications and patents referred to herein are incorporated by reference in their entirety. Unless otherwise specified, a reference to a particular compound includes all ionic, salt, solvate (e.g., hydrate), protected forms, prodrugs, and other stereoisomers thereof, isomeric forms, including racemic and other mixtures thereof. The invention provides the first products to put these components together to act in a synergistic manner in men's formulations. The invention also provides for the very first time the unexpected reduction of the DNA sperm fragmentation by the combination described herein:

The term "aromatase inhibitors" is used herein to refer to reversible or irreversible aromatase inhibitors including but not limited to natural flavanoids or synthetic products such products as anastrozole and exemestane (which is sold as Aromasin and is chemically described as 6-methylenandrosta-1,4-diene-3,17-dione), analogues or derivatives thereof such as those described in U.S. Pat. Nos. 4,808,616, 4,876,045 and 4,904,650, the teachings of which are incorporated herein in their entirety.

As used herein, "about" will mean up to plus or minus 5% of the particular term.

As used herein, "consisting essentially of" refers to excluding other active ingredients but including excipients.

The term "carnitine," except as individually recited, includes all pharmaceutically acceptable forms of carnitine including but not limited to l-carnintine or a prodrug thereof, acetyl-L-carnitine and propionyl-L-carnitine in form of HCl salt, in general alkanoyl L-carnitines such as isovaleryl-L-carnitine, hexanoly-L-carnitine, octanoyl-L-carnitine, myristoyl-L-carnitine, palmitoyl-L-carnitine, stearoyl-L-carnitine.

By "Fertilization Attempt" it is meant any process that facilitates fusion of the sperm and egg. Such term includes natural as well as medical procedures that facilitate embryonic development and pregnancy including but not limited to IUI, IVF and ICSI.

The term "folic acid or folate" (sometimes known as vitamin B9) is meant to include the synthetic form of the vitamin, in hydrate or salt forms with metal ions such as sodium, zinc etc.

The term "lycopene" is meant the red pigment in tomatoes in its pharmaceutically acceptable organic or inorganic form, which contains a $C_{40}$ open-chain hydrocarbon carotenoid with any of its 11 conjugated double bonds being available for the formation of cis and trans-geometrical isomers.

By the term "Reactive Molecular Species ("RMS")" it is meant to include Reactive Oxygen Species ("ROS"), Reactive Nitrogen Species ("RNS") and other reactive heteroatom species that can incapacitate sperm ability to fertilize an egg, preferably ROS as the most evaluated reactive moieties.

The term "selenium" is meant to include elemental, all inorganic and organic forms of selenium such as sodium selenite and sodium selenate, selenomethionine, selenocysteine, methyselenocysteine, methylselenol, amino acid chelates, yeast, and kelp bound selenium.

By the term "substantially free" it is meant that the final product is free of any traces of the identified ingredient to the extend that it could be detected by general quantitative assays known in the art for detection of such ingredient in the final product or if detected, it is in residual content of the ingredient and in principle only attributable to impurities.

The term "treatment" or "therapy" as used herein in the context of treating a condition to the extent that a positive clinical benefit is observed. Thus, a course of therapy includes prophylactic treatment, and further pertains generally to the therapy of a human subject. For example, the treatment of sperm oxidative stress and/or male infertility associated with sperm oxidative stress includes a reduction in the rate of production, rate of proliferation or the concentration of ROS in sperm cells, which can result in a halt in the rate of infertility. Treatment includes combination treatments and therapies, in which two or more treatments or therapies modalities are combined, for example, sequentially or simultaneously. Examples of treatments and therapies include, but are not limited to, antioxidant combination therapy with or without the use of anti-inflammatory agents, surgery, employing ART and/or other drug treatments generally known to improve rate of pregnancy.

The term "therapeutically-effective amount," as used herein, pertains to that amount of an active compound, or a material, composition or dosage form comprising an antioxidant, which is effective for producing the desired therapeutic effect, commensurate with a reasonable benefit/risk ratio to avoid excess concentration of such drugs to the extent that it would neutralize its expected therapeutic effects.

The term "vitamin C and/or its derivatives," except as individually recited, is meant to include ascorbic acid, a mineral ascorbate or a multi-mineral ascorbate, calcium ascorbate, magnesium ascorbate, zinc ascorbate, potassium ascorbate, sodium ascorbate, molybdenum ascorbate, chromium ascorbate, vitamin C Complex, Ascorbyl palmitate.

The term "vitamin E and/or its derivatives" is meant to include all variations of vitamin E, including but not limited the eight antioxidants commonly known as vitamin E; four tocopherols (alpha-, beta-, gamma-, and delta-) and four tocotrienols (alpha-, beta-, gamma-, and delta-).

The term "zinc" is meant to include all variations of zinc including but not limited to elemental zinc, zinc sulphate, zinc picolinate, zinc citrate, zinc acetate, zinc glycerate, and zinc monomethionine.

The invention provides a combination therapy for improving fertility in mammals particularly among those suffering from excess oxidative stress at their reproductive cell levels.

At least one aspect of the present invention provides treating infertility among any mammal including but not limited to land and aquatic animals such as primates, horses, donkeys, sheep, cats, dogs, pigs etc. In a more preferred embodiment, the mammal is a male human, horse or cow and in the most preferred embodiment the mammal is human.

In another aspect of the present invention the presently disclosed treatment reduces male infertility associated with sperm oxidative stress. The invention provides a scientifically validated nutritional blend for mammalian male to reduce sperm oxidative stress and infertility associated with such condition and further improve the sperm genomic integrity. The present combination of vitamins, minerals and amino acids reduces overall fragmentation of sperm cells and further secure higher rate of pregnancy among mammalian couples whose male counterpart suffers from infertility.

Those of ordinary skill in the art understand that sperm is highly susceptible to free radical or oxidative damage from environmental toxicants and natural aging. In at least one embodiment of the present invention vitamins C and E, zinc, and selenium, all of which are potent antioxidants that help improve sperm counts and quality, are used to neutralize the formation of excess ROS and maintain normal DNA makeup. Zinc and B vitamins (B6, B12 and folate) are critical nutrients in male reproductive systems for hormone metabolism, sperm formation and motility. However, synergistic combination of such ingredients for purposes of treating male infertility secondary to SOS has not been clinically proven. At least one aspect of the present invention, describes a profertility combination of such ingredients for treating male infertility associated with SOS.

In another aspect, the profertility combination of the present invention employs a source of carnitine. Such source includes L-carnitine, acetyl-L-carnitine or priopionyl-L-carnitine and all pharmaceutically acceptable salts thereof. The preferred embodiment of this aspect of the invention employs priopionyl-L-carnitine, hydrochloride, fummurate or tarterate salts thereof.

Another aspect of the present invention provides for a component that would have a synergistic action of the combinations. The distinct combinations are useful for couples who have failed to produce a healthy fertilized oocyte during at least a period ranging from three (3) to six (6) months prior to any fertilization attempts. Such couples generally include male subjects exposed to occupational toxic agents such as styrene, as well as those who may be subject to environmental, chemical, radiation, and heat exposure.

In one embodiment, the male human subject of the present invention is selected from the group consisting of a subject with increased levels of sperm DNA oxidation, reduced fertility of unknown origin; a subject having undergone vasectomy reversal; a subject with a reproductive tract infection such as epididymitis; and a subject having a varicocele.

Previous human studies assessing male subjects with increased levels of malondialdehyde or other biochemical markers of oxidative stress; a smoker; a subject with reduced fertility, including reduced fertility due to poor sperm motility have all failed to substantiate the use of other antioxidants' combinations in treating DNA fragmentation secondary to sperm oxidative stress. See Tremellen supra.

The present inventor has unexpectedly discovered that the instantly claimed blend of antioxidants drastically reduce sperm DNA fragmentation from the pretreatment baseline and increase rate of pregnancy.

Methods are known in the art for assessing the extent of free radical damage to sperm. For example, the thiobarbituric acid reactive substances ("TBARs") assay (which involves the measurement of malondialdehyde, a marker of sperm membrane oxidation) or LPO-856 spectrophotometric assay may be used. These methods are described for example in Gomez et al International Journal of Andrology 21(2), 81-96 (1998). Other methods include measurement of DNA Fragmentation Index ("DFI") using SCSA, SCD test, DBD-FISH test, and 8-OH-dG Assay.

In one embodiment, the administration of the present combination therapy to the subject results in a reduction in free radical damage to sperm's DNA of at least 2.5%, 5%, 8%, 10%, 12.5%, 15%, preferably 20% and most preferably 30%, when measured by a suitable sperm parameter analysis, preferably evaluated or expressed as DFI. In at least another embodiment, the administration of the present combination therapy to the male subjects results in a significant improvement in the degree of DNA damage secondary to SOS, when compared to the subject's own pretreatment values, by at least 1, 2.5%, 5%, 8%, 10%, 12.5%, 15%, 20%, 30%, and preferably 50%, wherein such improvement advances the pregnancy of a female partner. In a preferred embodiment, the administration of the antioxidant composition to a male subject results in a reduction in pretreatment baseline levels of the subject's DFI measurement by at least an absolute 2.5% (i.e. the actual difference in DFI measurement before and after the combination therapy).

The anti-oxidant agent in the various embodiments of the present invention may be one or more individual antioxidant (s). In this regard, an antioxidant is a molecule that can directly or indirectly reduce the damaging effects of oxygen and/or free-radicals in cells, and includes molecules that react with oxygen, or molecules that may protect against, and/or react with, a free radical.

In one embodiment, the anti-oxidant agent is selected from one or more of the group consisting of a vitamin C; vitamin E; β-carotenoid, including lycopene (a carotenoid derived from the tomato), lutein; a folic acid or derivative, selenium; zinc; L-carnitine, a prodrug thereof such as propionyl-L-carnitine; acety-L-carnitine; N-acetylcysteine; glutathione; gluthathionine; pyruvate; Coenzyme Q10, astaxanthin and hypotaurine; alpha-lipoic acid or a salt (if applicable), or a pharmaceutically acceptable derivative of any of the aforementioned agents. Other anti-oxidants are generally as described in Agarwal et al, *Role of Antioxidants in Treatment of Male Infertility: an Overview of the Literature*, Reproductive Biomedicine Online, 8(6), 616-62 (2004). Compounds such as gluthathione, astaxanthin or Coenzyme Q10 may be administered parenterally to enhance the ultimate clinical antioxidation.

The effective amount of the one or more anti-oxidant agents in the various embodiments of the present invention is not particularly limited, so long as it has the desired or therapeutic effect, and will depend upon the particular anti-oxidant (s) administered. In a preferred embodiment, the present invention contains tablets having vitamin E (d-alpha-tocopheryl acetate) in ranges of 50 to 1500 I.U., with a usual range of 200 to 1200 I.U., and typically 200 to 800 I.U.; vitamin C (ascorbic acid, or a salt thereof) in ranges of 10 to 1000 mg, with a usual range of 50 to 500 mg and typically 90 to 200 or 400 mg; selenium in ranges of 10 to 250 µg; zinc in amounts of about 5 to 100 mg; folic acid in amounts of about 0.1-1 mg; lycopene in amounts of about 0.5 to 20 mg, with usual ranges of 1 to 10 mg, a carnitine source in amounts of about 1 to 5 grams, with a usual range of 2 to 3 grams; and optionally glutathione in amounts of 100 to 1000 mg, with a usual range of 400 to 600 mg, preferably administered parenterally. In another aspect of this invention, the combination is supplemented with alpha-lipoic acid in amounts of about 50 to 600 mg.

In another aspect of the present invention, the combination therapy can optionally be supplemented with an aromatase inhibitor. Preferred aromatase inhibitor agents include natural and synthetic compounds that are able to modulate and reduce the activity of Aromatase, an enzyme found in the liver, which is responsible for the conversion of the androgens such as androstendione and testosterone into the estrogens such as estrone and estradiol. By inhibiting aromatase the body produces less estrogen and maintains a higher testosterone state. Suitable aromatase inhibitors include natural flavanoids such as chrysin, apigenin, indole-3-carbinols or synthetic compounds including but not limited to aminoglutethimide, anastrozole or 6-methylenandrosta-1,4-diene-3,17-dione.

In another embodiment, the anti-oxidant agent administered to the subject is a combination of the following anti-oxidant agents: vitamin C, vitamin E, selenium, zinc, and propionyl-L-carnitine. In yet another embodiment, the combination of the anti-oxidant agents consists essentially of vitamin C, vitamin E, selenium, zinc, propionyl-L-carnitine and folic acid. In yet another embodiment, the combination of the anti-oxidant agents consists of vitamin C, vitamin E, selenium, zinc, propionyl-L-carnitine and lycopene. In yet another embodiment, the combination of the anti-oxidant agents consists essentially of vitamin C, vitamin E, selenium, zinc, L-carnitine, folic acid and lycopene. In yet another embodiment, the combination of the anti-oxidant agents consists of vitamin C, vitamin E, selenium, zinc, acetyl-L-carnitine, folic acid and lycopene, and suitable excipients. In the most preferred embodiment, the combination of the anti-oxidant agents consists of vitamin C, vitamin E, selenium, zinc, acetyl-L-carnitine, proionyl-L-carnitine, folate or folic acid and lycopene and suitable excipients.

A suitable formulation (referred to as the Fertilix™ formulation) contains vitamin E (d-alpha-tocopheryl acetate) vitamin C (ascorbic acid or a salt thereof), selenium, zinc, folate or folic acid, lycopene, propionyl-L-carnitine, and acetyl-L-carnitine.

At least one embodiment of such formulation essentially contains vitamin E (d-alpha-tocopheryl acetate) 200 I.U.; vitamin C (ascorbic acid or a salt thereof) 90-200 mg, selenium 55 µg, zinc 15 mg, folate or folic acid 0.5 mg, lycopene 5 mg, propionyl-L-carnitine 500 mg, and acetyl-L-carnitine 1 gram. Another embodiment contains vitamin C (ascorbic acid or a salt thereof) in amount of 90 mg. Yet in another embodiment, the formulation further contains lipoic acid in amount of 60 mg.

In one embodiment, the duration for the treatment is at least for six (6) weeks to about twelve (12) months. In another embodiment, the duration of the therapy is for three (3) months prior any fertilization attempts. In further embodiments, the duration of the treatment regime is for six (6) months prior any fertilization attempts. In this regard, a suitable therapy for either of the following formulations is two administrations per day of one of the combinations, formulations, or compositions described above for a period of at least three (3) months prior to any fertilization attempts. However, it will be appreciated that the administration of the disclosed formulation and the other agents in the various embodiments of the present invention may be within any time and frequency suitable to produce the desired effect.

The anti-oxidant and the other agents of the present invention include those suitable for oral, nasal, topical (including buccal and sublingual), rectal, vaginal and/or parenteral administration. Regardless of the route of administration selected, the combination of the ingredients are formulated into pharmaceutically-acceptable dosage forms by conventional methods known to those of skill in the art.

The amount of the active antioxidants which will be combined with a carrier material to produce a single dosage form will generally be that amount of the active ingredient(s) which is the optimal dose effective to produce the therapeutic effect, herein as measured by DFI.

Methods of preparing pharmaceutical formulations or compositions include the step of bringing the antioxidants and/or other suitable active ingredients into association with the carrier and, optionally, one or more accessory ingredients. In general, the formulations are prepared by uniformly and intimately bringing the active ingredient(s) into association with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, microparticles, nanoparticles or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredient(s).

In solid dosage forms of the invention for oral administration (capsules, tablets, pills, powders, granules and the like), the prodrug(s), antioxidant(s) and/or other suitable pharmaceutically active ingredient(s) (in their micronized, microparticle or nanoparticle forms) is/are mixed with one or more pharmaceutically-acceptable carriers, such as cellulose, magnesium stearate, silicon dioxide, sodium citrate or dicalcium phosphate, and/or any of the following: (1) fillers or extenders, such as starches, lactose, sucrose, glucose, mannitol, cellulose and/or silicic acid; (2) binders, such as, for example, carboxymethyl-cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, silicon dioxide, other types of silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents.

In the case of capsules, tablets and pills, the pharmaceutical compositions may also comprise buffering agents. Solid compositions of a similar type may also be employed as fillers in soft and hard-filled gelatin capsules using such excipients as cellulose, magnesium stearate, silicon dioxide, lactose or milk sugars, with or without high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient(s) moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow, extended or controlled release of the desired antioxident(s) therein using, for example, hydroxypropylmethyl cellulose in varying proportions to provide the desired release profile, other polymer matrices, nanoparticles and/or microspheres. They may be sterilized by for example, filtration through a bacteria-retaining filter.

Liquid dosage forms for oral administration of the active ingredient(s) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethylacetate, butyl alcohol, benzyl benzoate, propylene glycol, glycol, oils (in particular, cottonseed, groundnut, corn, germ, olive, castor and sesame oils), glycerol, amyl alcohol, tetrahydrofuryl polyethylene glycols and fatty acid esters of sorbitan, and mixtures thereof.

Besides inert diluents the oral compositions can also include adjuvants such as wetting agents, emulsifying and suspending agents, sweetening, flavoring, coloring, perfuming and preservative agents. Suspensions, in addition to the active ingredient(s), may contain suspending agents as, for example, ethoxylated alcohols, polyoxyethylene sorbitol and sorbitan esters, microcrystalline cellulose, bentonite, agar and tragacanth, and mixtures thereof.

Dosage forms for the topical or transdermal administration of the active ingredient(s) include powders sprays, ointments, pastes, creams, lotions, gels, solutions, patches and inhalants. The active ingredient(s) may be mixed under sterile conditions with pharmaceutically-acceptable carrier, and with any buffers, or propellants which may be required.

The ointments, pastes, creams and gels may contain, in addition to the active ingredient(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient(s), excipients such as lactose, talc, silicic acid, aluminum hydroxide, calcium silicates and polyamide powder, or mixtures of these substances. Sprays and inhalers can additionally contain customary propellants such as chlorofluorohydrocarbons and volatile unsubstituted hydrocarbons, such as butane and propane.

Compositions of the present invention may be administered in intranasal form via topical use of suitable intranasal vehicles, or via transdermal routes, using those forms of transdermal skin patches well known to those of ordinary skill in the art. A transdermal delivery system provides for continuous administration throughout the treatment regimen. Transdermal patches have the added advantage of providing controlled delivery of the active ingredient(s) to the body. Such dosage forms can be made by dissolving, dispersing or otherwise incorporating the active ingredient(s) in a proper medium, such as an elastomeric matrix material. Absorption enhancers can also be used to increase the flux of the active ingredient(s) across the skin. The rate of such flux can be controlled by either providing a rate-controlling membrane or dispersing the active ingredient(s) in a polymer matrix or gel.

Another mode of delivery for present combination of the present invention may be delivery via the use of targeting compounds. Accordingly a nanoparticulate or microparticulate blend of the antioxidant(s) in proper ratios may be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Pharmaceutical compositions of this invention suitable for parenteral administration comprise the antioxidant(s) in combination with one or more pharmaceutically-acceptable sterile isotonic aqueous or nonaqueous solutions, suspensions or emulsions, or sterile powders which may be reconstituted into sterile injectable solutions or dispersions just prior to use, which may contain the combination of the antioxidants, minerals and vitamins, buffers, solutes which render the formulation isotonic with the blood of the intended recipient or suspending or thickening agents.

Examples of suitable aqueous and nonaqueous carriers which may be employed in the pharmaceutical compositions of the invention include water, dextrose, ethanol, polyols (such as glycerol, propylene glycol, polyethylene glycol, and the like), and suitable mixtures thereof. Proper fluidity can be maintained, for example, by the use of coating materials, such as lecithin, by the maintenance of the required particle size, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

Injectable depot forms are made by forming microencapsule matrices of the antioxidant(s), minerals and vitamins in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly (orthoesters) and poly(anhydrides). The injectable materials can be sterilized for example, by filtration through a bacterial-retaining filter.

The pharmaceutical compositions of the present invention may also be used in the form of veterinary formulations for treating infertile cattle, herd, or other infertile mammals, including those adapted for the following: (1) oral administration, for example, drenches (aqueous or nonaqueous solutions or suspensions), tablets, boluses, powders, granules or pellets for admixture with feed stuffs, pastes for application to the tongue; (2) parenteral administration, for "ampule," by subcutaneous, intramuscular or intravenous injection as, for example, a sterile solution or suspension or, when appropriate, by injection where a suspension or solution is introduced to the animal; (3) topical application, for example, as a cream, ointment or spray applied to the skin; or any other methods fit to by those of ordinary skill in the art for administration to a region of interest.

Formulation of the agents of the present invention and their administration may be facilitated by an easy to use kit to ameliorate and assist patients to follow the treatment regimen. As discussed previously herein, the agents in the various embodiments of the present invention may be administered jointly or separately in the form of oral preparations (for example solid preparations such as tablets, capsules, granules or powders; liquid preparations such as syrup, emulsions or suspensions).

Compositions containing the anti-oxidant agent and the other agents separately or jointly in the various embodiments of the present invention may also contain a preservative, stabilizer, dispersing agent, pH controller or isotonic agent Examples of suitable preservatives in the various embodiments of the present invention are glycerin, propylene glycol, phenol or benzyl alcohol. Examples of suitable stabilizers in the various embodiments of the present invention are dextran, gelatin, or alpha-thioglycerin.

Examples of suitable dispersing agents in the various embodiments of the present invention include polyoxyethylene (20), sorbitan mono-oleate (Tween 80), sorbitan sesquioleate (Span 30), polyoxyethylene (160) polyoxypropylene (30) glycol (Pluronic F68) or polyoxyethylene hydrogenated castor oil 60. Examples of suitable pH controllers in the various embodiments of the present invention include hydrochloric acid, sodium hydroxide and the like. Examples of suitable isotonic agents are glucose, D-sorbitol or D-mannitol.

As discussed previously herein, the present invention is also suitable for reducing the generation of ROS in the male reproductive tract and/or semen. In this regard, the male reproductive tract will be understood to include the epididymis, the penis, the prostate gland, the seminal vesicles, the testes, the vas deferens and semen. Methods for determining the level of free radicals in the male reproductive tract are known in the art. For example, free radical production by sperm or seminal leukocytes can be measured directly using chemiluminescence assays known in the art. Alternatively, assays that measure free radical related damage to sperm lipid membrane may be used. For example, the TBARs assay (which involves the measurement of malondialdehyde, a marker of sperm membrane oxidation) or LPO-586 spectrophotometric assay may be used. These methods are described in Gomez et al (1998) International Journal of Andrology 21(2):81-96.

In one embodiment, the level of male fertility track is assessed by the way of suitable inflammatory indices. For example, one of ordinary skill in the art would with to assess the presence or absence of inflammatory cytokine, like one or more of IL-I, IL-6, IL-, TNF-$\alpha$ and Interferon-$\gamma$. Methods for determining the level of an inflammatory cytokine in the male reproductive tract are known in the art, such ELISA assays for detection of pro-inflammatory cytokines such as IL-I, IL-6, IL-8, TNF-$\alpha$ and Interferon-$\gamma$, as described in Depuydt et al. J Andrology 17(61), 699-707 (1996) or Maegawa et al J Reprod Immunology, 54, 33-42 (2002), and Nallella et al. Urology 64(5), 1010-3 (2004).

Those of ordinary skill in the art can also employ other methods of assessing the "sperm function." The term as used herein includes any key component of sperm physiology and includes swimming activity towards the oocyte (motility), ability to undergo capacitation to penetrate the oocyte's outer coat (zona pellucida) and fuse with the oocyte membrane, and maintenance of sperm DNA integrity to form a functional male pro-nucleus at syngamy. Methods for determining the level of sperm function are known in the art. For example, suitable methods are described in detail within the World Health Organization (WHO) laboratory manual for the examination of human semen and sperm-cervical mucous interaction. 4th edition. Cambridge University Press 1999.

In at least one embodiment of the present invention, the sperm DNA fragmentation is assessed by SCSA. Evenson D P, et al, *Relationship Between Assisted Reproductive Tech-* niques (*ART*) *outcome and Status of Chromatin Integrity as Measured by the Sperm Chromatin Structure Assay (SCSA)*. Hum. Reprod., 15, 1717-1722 (2000). At least one indicator of the clinical benefits of the claimed methodology is marked improvement of the DFI.

In principle, spermatozoa chromatin is different in nature from somatic cells chromatin. This difference is due to ploidy and DNA packaging, which is influenced by the replacement of histones in spermatocytes by transition proteins and then substitution of histone by protamine in spermatides. Green et al, *Synthesis and Processing of Mammalian Protamines and Transition Proteins*. Mol. Repr Dev 37, 255-263 (1994). Histones are the chief protein components of chromatin that coils around DNA enabling it to fit the large genomic information inside cell nuclei. Without histones, the unwound DNA in chromosomes would be very long. Replacement of histones by protamine are generally known to contribute to sperm's head condensation and DNA stabilization. See Id. Those of ordinary skill in the art can appreciate that DNA fragmentation levels above 30% as measured by SCSA are not compatible with initiation and maintenance of a term pregnancy. See Larson supra. SCSA test values, expressed as DFI, are significantly correlated with pregnancy rate in vivo and in vitro. In studies that included more than 25 couples undergoing in vitro fertilization and intracytoplasmic sperm injection cycles, no term pregnancy occurred when the DFI measurement was more than 27% in the semen samples utilized in these cycles. See Larson supra.

In the preferred embodiment of the present invention, baseline DFI is measured prior to the administration of the antioxidant regimen to assess a fertility capacity of male subjects. In the present invention, DFI values in combination with other subjective or objective signs of infertility would be used as the criteria to determine couples predisposition to failed pregnancy. Once study couples have undergone the baseline evaluation, they will receive a three (3) months course of therapy of the claimed antioxidant formulation in a kit containing other educational material regarding their therapy.

The effectiveness of the treatment course is then substantiated by statistically significant reduction in DFI and further the actual pregnancy of the couple's female subject. Those of ordinary skill in the art can appreciate measurements of other sperm parameters during the period of the trial to assess treatment efficacy. Such parameters can include sperm count, sperm density, motility, membrane integrity, testosterone or other hormonal levels if so desired, and other DNA damage techniques at various intervals including the entry period, 6 weeks, and/or 12 week time points. However, the actual clinical end point can be evaluated in view of other indicators including but not limited to fertilization rates among treatment group, embryo or blastocyst quality, number of viable embryos or blastocyst for transfer, number of miscarriages and the occurrence rate thereof.

An effective amount of the antioxidant agents and the other agents may be appropriately chosen, depending upon, for example, the type and extent of reduced fertility to be treated, the age and body weight of the subject, the DFI measurement, the frequency of administration, and the presence of other active agents. The instant antioxidant, mineral and vitamin combination, and/or the anti-aromatase agent may be administered to the subject separately or in combination via separate routes of administrations.

Accordingly, in another embodiment the present invention provides a combination product for improving sperm function in a male subject, the combination kit product including the following components: (a) a composition containing the present antioxidant, mineral and vitamin combination; and/or (b) an aromatase inhibitor agent, and/or (c) another adjuvant agent such as gluthothione or Coenzyme Q10 with (d) educational information and direction of use.

In yet another embodiment, the inventor describes the use of a carnitine source in the combinations described herein. L-carnitine, acetyl-L-carnitine and propionyl-L-carnitine are endogenous ligands that play essential role in transporting fatty acids into the mitochondria, where they are oxidized to produce energy. The carnitine pool is particularly important to spermatozoa as they are rich in mitochondria generating energy especially to support their motility. Carnitines are also scavengers of oxygen free radicals in mammalian tissues. Thus, the biochemical and antioxidant role of carnitines make them vitally important molecules in the overall health of the spermatozoa.

Propionyl-L-carnitine is known in the art to increase cellular levels of L-carnitine by binding to the enzyme carnitine acetyltransferase (CAT) which is subsequently converted into propionyl-coenzyme A and free carnitine. Propionyl-L-carnitine is also rapidly absorbed after oral administration reaching peak concentrations in about 1 hour followed by a rise in L-carnitine plasma levels 2-6 hours after the administration.

WO publication 03/084526 have previously shown the impact of such prodrugs in sperm motility and concentration. However, the acetyl-L-carnitine and propyl-L-carnitine alone or in combination have not been described in male prenatal compositions have not been described. In at least one aspect of the present invention, the inventors believe that the exogenous propionyl-L-carnitine supplementation alone will more effectively address any carnitine deficiency in infertile men.

The forgoing examples are used to further describe the invention employing at least one embodiment of the presently disclosed combination, the Fertilix™ profertility therapy Those of ordinary skill in the art can appreciate that patients who had received IVF before and during, as well as, those patients resorting to other fertilization attempts, would benefit from the presently disclosed treatment regimen by improving their embryonic quality and reducing the complications during the pregnancy term. At least one embodiment of the present invention focus the treatment regimen on the male partners. Yet another embodiment of the invention, include independently or simultaneously administering the regimen to the female partners.

With well over 3 million men currently experiencing male related infertility in the United States. Traditionally male infertility treatment has not endeavored to ameliorate the underlying cause of infertility but rather used "mechanical" techniques such as intra-uterine insemination or IVF-ICSI to bypass the defect in sperm function. While these two techniques are undeniably successful in a large proportion of patients, they simply do not work or have very limited efficiency in other couples. It is likely that in many cases, sperm DNA fragmentation is responsible for the poor pregnancy outcome despite ART treatment. The present invention provides treatments that can prophylactically treat sperm DNA fragmentation and is likely to boost both natural and ART related pregnancy rates.

A total of two (2) separate human trials are envisioned for further assessing the efficacy of the combination therapy instantly disclosed. Prior experiences with antioxidant combinations have not provided any evidence that antioxidant combinations can reduce sperm's DNA fragmentation secondary to oxidative stress. See Tremelton supra. Contrary to such scientific body of evidence, the present treatment regimen unexpectedly show a significant reduction of DFI after three (3) months of therapy.

In assessing the efficacy of other prior art antioxidant combinations, one of ordinary skill in the art would appreciate that even though the rate of pregnancy outcomes might have improved in the antioxidant treatment groups; the measured sperm parameters for the treatment group was not affected and the treatment had no effect on sperm concentration, motility or morphology. See Tremelton supra at pgs 219-220. Furthermore, the LPO-586 assay for lipid peroxidation damage did not detect any significant difference in levels of free radical damage to the sperm membrane of the subjects. See Id. In fact, prior art formulations failed to show a correlation between SOS or sperm DNA damage and pregnancy rates since the sperm DNA damage assays employed failed to show a difference between the treatment and the placebo groups. See Id.

The present invention provides a new combination of antioxidants with an unexpected reduction in sperm's DNA fragmentation due to local oxidative stress. Unexpected results extend to the inventors observation of improved quality of the sperm parameters, which when coupled with successful pregnancies, confirms the efficacy of Fertilix™ therapy in treating male infertility associated with SOS.

Example 1

First combination for men is prepared according to the following formula:

TABLE I

| | |
|---|---|
| d-alpha-tocopheryl acetate | 200 IU |
| Ascorbic acid | 200 mg |
| Selenium | 55 μg |
| Zinc | 15 mg |
| Folic acid | 0.5 mg |
| Lycopene | 5 mg |
| Propionyl-L-Carnitine | 0.5 g |
| Excipients | As needed |

Example 2

A second combination is prepared according to the following formula:

TABLE 2

| | |
|---|---|
| Vitamin E | 200 IU |
| Vitamin C | 200 mg |
| Selenium | 55 μg |
| Zinc | 15 mg |
| Folic acid | 0.5 mg |
| Lycopene | 5 mg |
| Acetyl-L-Carnitine | 1.0 g |
| Propionyl-L-Carnitine | 0.5 g |
| Excipients | As needed |

Example 3

Another formulation is prepared according to the following formula:

TABLE 3

| | |
|---|---|
| Vitamin E | 200 IU |
| Vitamin C | 200 mg |
| Selenium | 55 μg |
| Zinc | 15 mg |
| Folic acid | 0.5 mg |
| Lycopene | 5 mg |
| L-Carnitine | 1 g |
| Excipients | As needed |

Example 4

Another formulation is prepared according to the following formula:

TABLE 4

| | |
|---|---|
| Vitamin E | 200 IU |
| Vitamin C | 200 mg |
| Selenium | 55 μg |
| Zinc | 15 mg |
| Folic acid | 0.5 mg |
| Lycopene | 5 mg |
| L-Carnitine | 1.0 g |
| Acetyl-L-Carnitine | 0.5 g |
| Excipients | As needed |

Example 5

Another formulation is prepared according to the following formula:

TABLE 5

| | |
|---|---|
| Vitamin E | 200 IU |
| Vitamin C | 200 mg |
| Selenium | 55 μg |
| Zinc | 15 mg |
| Folic acid | 0.5 mg |
| Lycopene | 5 mg |
| L-Carnitine | 1.0 g |
| Propionyl-L-Carnitine | 0.5 g |
| Excipients | As needed |

Example 6

Another formulation for men is prepared according to the following formula:

TABLE 6

| | |
|---|---|
| Vitamin E | 200 IU |
| Ascorbic acid | 90 mg |
| Selenium | 55 μg |
| Zinc | 15 mg |
| Folic acid | 0.5 mg |
| Lycopene | 5 mg |
| Propionyl-L-Carnitine | 0.5 g |
| Excipients | As needed |

Example 7

Yet, another formulation is prepared according to the following formula:

TABLE 7

| | |
|---|---|
| Vitamin E | 200 IU |
| Vitamin C | 90 mg |
| Selenium | 55 μg |
| Zinc | 15 mg |
| Folic acid | 0.5 mg |

TABLE 7-continued

|  |  |
|---|---|
| Lycopene | 5 mg |
| Acetyl-L-Carnitine | 0.75 g |
| Propionyl-L-Carnitine | 0.5 g |
| Excipients | As needed |

Example 8

Another formulation is prepared according to the following formula:

TABLE 8

|  |  |
|---|---|
| Vitamin E | 200 IU |
| Vitamin C | 90 mg |
| Selenium | 55 µg |
| Zinc | 15 mg |
| Folic acid | 0.5 mg |
| Lycopene | 5 mg |
| L-Carnitine | 1 g |
| Excipients | As needed |

Example 9

Another formulation is prepared according to the following formula:

TABLE 9

|  |  |
|---|---|
| Vitamin E | 200 IU |
| Vitamin C | 90 mg |
| Selenium | 55 µg |
| Zinc | 15 mg |
| Folic acid | 0.5 mg |
| Lycopene | 5 mg |
| L-Carnitine | 1.0 g |
| Acetyl-L-Carnitine | 0.5 g |
| Excipients | As needed |

Example 10

Another formulation is prepared according to the following formula:

TABLE 10

|  |  |
|---|---|
| Vitamin E | 200 IU |
| Vitamin C | 90 mg |
| Selenium | 55 µg |
| Zinc | 15 mg |
| Folic acid | 0.5 mg |
| Lycopene | 5 mg |
| L-Carnitine | 1.0 g |
| Propionyl-L-Carnitine | 0.5 g |
| Excipients | As needed |

Example 11

Couple DP underwent multiple cycles of IVF that resulted in no viable pregnancy. The sperm DNA fragmentation index of the male subject was measured by SCSA to be 27%. The male partner then started on a twice a day combination therapy described in Example 3, Table 3 for a period of three (3) months. The combination contained vitamin E (d-alpha-tocopheryl acetate) 200 I.U., vitamin C 200 mg, selenium 55 µg, zinc 15 mg, folic acid 0.1 mg, L-carnitine 1 g, and lycopene 5 mg.

The post treatment DFI measurement showed an absolute 7.4% reduction in the DFI levels amounting to a 27.4% improvement from the pretreatment baseline DFI levels. Upon completion of the therapeutic regimen, even though no in vitro embryo assessment was done, the female partner became pregnant and gave birth to a healthy child nine (9) months following the termination of the anti-oxidant therapy.

Example 12

In another trial, the same couple used the same treatment regimen as described in Example 2. The male's sperm DFI measurement indicated a free radical damage of 39.6% prior to the initiation of the antioxidant combination therapy. The DFI measurement at least three (3) months after the initial treatment was measured as 27.2 showing an unexpected improvement of at least an absolute 12.4% reduction in DNA fragmentation index amounting to a 31% improvement from the pretreatment baseline DFI levels. While no in vitro embryo assessment was done, the female partner became pregnant and gave birth to a healthy child nine (9) months thereafter.

While the invention has been described with references to specific embodiments, modifications and variations of the invention may be construed without departing from the scope of the invention, which is defined in the following claims.

The invention claimed is:

1. A method of treating male infertility secondary to sperm oxidative stress in a patient suffering from sperm DNA fragmentation Index of >30%, comprising administering to said patient a composition for a period of up to three months wherein said composition comprising, vitamin E; vitamin C; selenium; zinc; lycopene or lipoic acid; at least one source of carnitine, a folate or folic acid or suitable salts thereof and a pharmaceutically suitable carrier or excipient, and wherein the composition is substantially free of any traces of vitamin A, vitamin K, and garlic, and further wherein the DNA fragmentation Index is reduced by at least 2.5% after the three month time period.

2. The method of claim 1, wherein said folic acid is administered in an amount ranging from about 0.1 mg to about 5.0 mg.

3. The method of claim 1, wherein the vitamin C source is ascorbic acid and vitamin E is selected from the group consisting of a tocopherol or a tocotrienol or a combination thereof.

4. The method of claim 1, wherein the vitamin C source is a vitamin C derivative selected from the group consisting of calcium ascorbate, magnesium ascorbate, zinc ascorbate, potassium ascorbate, sodium ascorbate, a mineral ascorbate or a multi-mineral ascorbate and combinations thereof.

5. The method of claim 3, wherein the vitamin C is administered to the patient in an amount ranging from about 10 mg to about 1000 mg.

6. The method of claim 4, wherein the composition is in a tablet dosage form selected from the group consisting of an immediate release tablet, an extended or pulsatile release tablet, a chewable tablet, a chewable lozenge, a quick chew, a quick dissolve and combinations thereof.

7. A method of prophylactically treating a disease associated with increased levels of reactive oxidative species in sperm comprising administering to a male subject in need thereof, a composition comprising an effective amount of vitamin E; vitamin C; selenium; zinc; lycopene or lipoic acid; at least one source of carnitine, a folate or folic acid or suitable salts thereof, as the sole active ingredients and a pharmaceutically suitable carrier or excipient wherein the composition is substantially free of vitamin A, vitamin K, garlic.

8. A method of prophylactically treating formation of a nonviable zygote comprising administering to a male subject in need thereof, a composition comprising an effective amount of vitamin E; vitamin C; selenium; zinc; lycopene or lipoic acid; at least one source of carnitine, a folate or folic acid or suitable salts thereof, as the sole active ingredients and a pharmaceutically suitable carrier or excipient wherein the composition is substantially free of vitamin A, vitamin K, garlic.

9. The composition consisting of the following active ingredients:
- (a) from 200 I.U. to 600 I.U. of vitamin E selected from the group consisting of alpha-tocopherol, beta-tocopherol, gamma-tocopherol, delta-tocopherol, alpha-tocotrienol, beta-tocotrienol, gamma-tocopherol, delta-tocopherol, and any combinations thereof;
- (b) from 75 mg to 100 mg vitamin C;
- (c) from 45 µg to 60 µg selenium;
- (d) from 5 mg to 15 mg zinc in suitable salt form;
- (e) from 0.25 mg to 0.60 mg of folic acid;
- (f) from 5 mg to 20 mg lycopene;
- (g) from 100 mg to 800 mg propionyl-L-carnitine; and
- (h) from 100 mg to 800 mg acetyl-L-carnitine, and
- at least one pharmaceutically suitable carrier or excipient.

10. A composition consisting of the active ingredients:
- (a) from about 50 I.U. to about 1000 I.U. of vitamin E selected from the group consisting of alpha-tocopherol, beta-tocopherol, gamma-tocopherol, delta-tocopherol, alpha-tocotrienol, beta-tocotrienol, gamma-tocopherol, delta-tocopherol, and any combinations thereof;
- (b) from about 50 mg to about 400 mg vitamin C;
- (c) from about 45 µg to about 65 µg selenium;
- (d) from about 10 mg to about 30 mg zinc in its suitable salt form,
- (e) from about 0.25 mg to about 0.75 mg of folic acid;
- (f) from about 2.5 mg to about 20 mg lycopene;
- (g) from about 100 mg to about 2000 mg of a carnitine source selected from the group consisting of propionyl-L-carnitine; acetyl-L-carnitine; or a combination thereof; and at least one pharmaceutically suitable carrier or excipient.

11. A composition consisting of the active ingredients: (a) from about 50 I.U. to about 1000 I.U. of vitamin E selected from the group consisting of alpha-tocopherol, beta-tocopherol, gamma-tocopherol, delta-tocopherol, alpha-tocotrienol, beta-tocotrienol, gamma-tocopherol, delta-tocopherol, and any combinations thereof (b) from about 50 mg to about 400 mg vitamin C; (c) from about 45 µg to about 65 µg selenium: (d) from about 10 mg to about 30 mg zinc in its suitable salt form, (e) from about 0.25 mg to about 0.75 mg of folic acid; (f) from about 2.5 mg to about 20 mg lycopene; (g) from about 100 mg to about 2000 mg of a carnitine source selected from the group consisting of propionyl-L-carnitine; acetyl-L-carnitine; or a combination thereof; (h) N-acetyl-cysteine and at least one pharmaceutically suitable carrier or excipient.

* * * * *

UNITED STATES PATENT AND TRADEMARK OFFICE
CERTIFICATE OF CORRECTION

PATENT NO. : 8,377,454 B2
APPLICATION NO. : 12/771928
DATED : February 19, 2013
INVENTOR(S) : Parviz Gharagozloo It is certified that error appears in the above-identified patent and that said Letters Patent is hereby corrected as shown below:

In the Claims:

Claim 1

At column 20, line 33, please delete "comprising" and replace it with --comprises--

At column 20, line 35, please replace the "," after "carnitine" with a --;--

So that the claim reads:

1. A method of treating male infertility secondary to sperm oxidative stress in a patient suffering from sperm DNA fragmentation Index of >30%, comprising administering to said patient a composition for a period of up to three months wherein said composition comprises vitamin E; vitamin C; selenium; zinc; lycopene or lipoic acid; at least one source of carnitine; a folate or folic acid or suitable salts thereof and a pharmaceutically suitable carrier or excipient, and wherein the composition is substantially free of any traces of vitamin A, vitamin K, and garlic, and further wherein the DNA fragmentation Index is reduced by at least 2.5 % after the three month time period.

Claim 3

At column 20, line 46, please delete "a tocopherol or a tocotrienol or a combination" and replace it with --a tocopherol, a tocotrienol and a combination--

So that the claim reads:

3. The method of claim 1, wherein the vitamin C source is ascorbic acid and vitamin E is selected from the group consisting of a tocopherol, a tocotrienol and a combination thereof.

Signed and Sealed this
Fifteenth Day of April, 2014

Michelle K. Lee
*Deputy Director of the United States Patent and Trademark Office*

Claim 7

At column 20, line 66, please replace the "," after "carnitine" with a --;--

At column 21, line 2, insert the word --and-- before the word "garlic"

So that the claim reads:

7. A method of prophylactically treating a disease associated with increased levels of reactive oxidative species in sperm comprising administering to a male subject in need thereof, a composition comprising an effective amount of vitamin E; vitamin C; selenium; zinc; lycopene or lipoic acid; at least one source of carnitine; a folate or folic acid or suitable salts thereof, as the sole active ingredients and a pharmaceutically suitable carrier or excipient wherein the composition is substantially free of vitamin A, vitamin K, and garlic.

Claim 8

At column 21, line 3, please delete "an" and replace it with --a--

At column 21, line 7, please replace the "," after "carnitine" with a --;--

At column 21, line 11, insert the word --and-- before the word "garlic"

So that the claim reads:

8. A method of prophylactically treating formation of a nonviable zygote comprising administering to a male subject in need thereof, a composition comprising an effect amount of vitamin E; vitamin C; selenium; zinc; lycopene or lipoic acid; at least one source of carnitine; a folate or folic acid or suitable salts thereof, as the sole active ingredients and a pharmaceutically suitable carrier or excipient where the composition is substantially free of vitamin A, vitamin K, and garlic.

Claim 9

At column 21, line 12, please delete the first "The" and replace it with --A--

At column 21, line 24, please delete the word "and"

So that the claim reads in part:

9. A composition consisting of the following active ingredients...(g) from 100 mg to 800 mg propionyl-L-carnitine; (h) from 100 mg to 800 mg acetyl-L-carnitine, and at least one pharmaceutically suitable carrier or excipient.

Claim 10

At column 22, lines 10-12, please delete "propionyl-L-carnitine; acetyl-L-carnitine; or a combination thereof;" and replace it with --propionyl-L-carnitine, acetyl-L-carnitine, and a combination thereof;--

So that the claim reads in part:

...(g) from about 100 mg to about 2000 mg of a carnitine source selected from the group consisting of propionyl-L-carnitine, acetyl-L-carnitine, and a combination thereof; and at least one pharmaceutically suitable carrier or excipient.

Claim 11

At column 22, lines 25-26, please delete "propionyl-L-carnitine; acetyl-L-carnitine; or a combination thereof;" and replace it with --propionyl-L-carnitine, acetyl-L-carnitine, and a combination thereof;--

So that the claim reads in part:

...(g) from about 100 mg to about 2000 mg of a carnitine source selected from the group consisting of propionyl-L-carnitine, acetyl-L-carnitine, and a combination thereof; (h) N-acetyl-cysteine and at least one pharmaceutically suitable carrier or excipient.